(12) United States Patent
Liu et al.

(10) Patent No.: US 7,569,057 B2
(45) Date of Patent: Aug. 4, 2009

(54) IMPULSIVE PERCUSSION INSTRUMENTS FOR ENDPLATE PREPARATION

(75) Inventors: Mingyan Liu, Bourg la Reine (FR); Loic Josse, Palaja (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 629 days.

(21) Appl. No.: 10/937,159

(22) Filed: Sep. 9, 2004

(65) Prior Publication Data

US 2005/0065529 A1 Mar. 24, 2005

(30) Foreign Application Priority Data

Sep. 11, 2003 (EP) .................................. 03292241

(51) Int. Cl.
*A61B 17/32* (2006.01)
(52) U.S. Cl. .......................... 606/79; 606/171; 606/173
(58) Field of Classification Search .................. 606/79, 606/80, 83–86, 171, 168, 173, 182; 30/392–394, 30/182, 186, 187, 209, 210, 216–220
See application file for complete search history.

(56) References Cited

U.S. PATENT DOCUMENTS

| | | | |
|---|---|---|---|
| 2,100,319 A | | 11/1937 | Brown et al. |
| 2,124,024 A | | 7/1938 | Alkin |
| 2,588,006 A | | 3/1952 | Hufnagel |
| 3,561,429 A | * | 2/1971 | Jewett et al. ................ 600/565 |
| 3,995,619 A | * | 12/1976 | Glatzer ....................... 600/550 |
| 4,108,182 A | * | 8/1978 | Hartman et al. ............. 606/171 |
| 4,210,146 A | * | 7/1980 | Banko ......................... 606/171 |
| 4,246,902 A | * | 1/1981 | Martinez ..................... 604/22 |
| 4,298,074 A | | 11/1981 | Mattchen |
| 4,299,571 A | * | 11/1981 | McSpadden ................ 433/102 |
| 4,358,230 A | * | 11/1982 | Rohlin ........................ 408/124 |
| 4,512,344 A | * | 4/1985 | Barber ........................ 606/79 |
| 4,589,414 A | * | 5/1986 | Yoshida et al. .............. 606/171 |
| 4,782,588 A | * | 11/1988 | Jangaard ..................... 29/810 |
| 5,057,112 A | | 10/1991 | Sherman et al. |
| 5,152,352 A | | 10/1992 | Mandanis |
| 5,269,794 A | * | 12/1993 | Rexroth ...................... 606/180 |
| 5,324,297 A | | 6/1994 | Hood et al. |

(Continued)

FOREIGN PATENT DOCUMENTS

WO   WO 98/04202   2/1998

(Continued)

*Primary Examiner*—Eduardo C Robert
*Assistant Examiner*—Tara R George

(57) ABSTRACT

A hand-held instrument, with a rotary power input to a camshaft, has cam and follower arrangement to provide a reciprocating shaft output. A cutter is provided on the output shaft. In one example, rotating cam percussion is transmitted to the cutter by engaging the cutter with the tissue to be cut, and pushing the instrument forward toward the cutter. In another example, rotating cam percussion is transmitted to the cutter by engaging the cutter with the tissue to be cut, and pulling the instrument back toward the user while maintaining engagement of the cutter with the tissue. In both examples, the cutter remains in idle condition until an axially directed load, forward in the one example, or backward on the other example, is placed on the cutter by moving the instrument forward or backward, respectively, while the camshaft is rotating. A distractor with frame is used to spread and maintain space between vertebral bodies, enabling entrance of the cutter.

41 Claims, 21 Drawing Sheets

U.S. PATENT DOCUMENTS

| | | | |
|---|---|---|---|
| 5,352,230 A | 10/1994 | Hood | |
| 5,431,658 A | 7/1995 | Moskovich | |
| 5,509,918 A * | 4/1996 | Romano | 606/80 |
| 5,571,109 A | 11/1996 | Bertagnoli | |
| 5,591,170 A * | 1/1997 | Spievack et al. | 606/82 |
| 5,618,293 A * | 4/1997 | Sample et al. | 606/170 |
| 5,632,759 A * | 5/1997 | Rexroth | 606/180 |
| 5,741,263 A * | 4/1998 | Umber et al. | 606/80 |
| 5,782,836 A * | 7/1998 | Umber et al. | 606/79 |
| 6,083,228 A | 7/2000 | Michelson | |
| 6,209,659 B1 | 4/2001 | Blessing | |
| 6,224,599 B1 | 5/2001 | Baynham et al. | |
| 6,233,833 B1 * | 5/2001 | Grant et al. | 30/392 |
| 6,508,151 B1 * | 1/2003 | Neitzell | 83/34 |
| 6,530,936 B1 * | 3/2003 | Yun | 606/167 |
| 6,742,266 B2 * | 6/2004 | Splane, Jr. | 30/392 |
| 6,755,837 B2 * | 6/2004 | Ebner | 606/84 |
| 6,958,071 B2 * | 10/2005 | Carusillo et al. | 606/180 |
| 2001/0037114 A1 * | 11/2001 | Dinger et al. | 606/85 |
| 2004/0010258 A1 * | 1/2004 | Carusillo et al. | 606/79 |
| 2004/0059338 A1 * | 3/2004 | Ebner | 606/84 |
| 2005/0113838 A1 * | 5/2005 | Phillips et al. | 606/80 |
| 2006/0129160 A1 * | 6/2006 | Liu et al. | 606/85 |

FOREIGN PATENT DOCUMENTS

WO     WO 01/28468 A1     4/2001

* cited by examiner

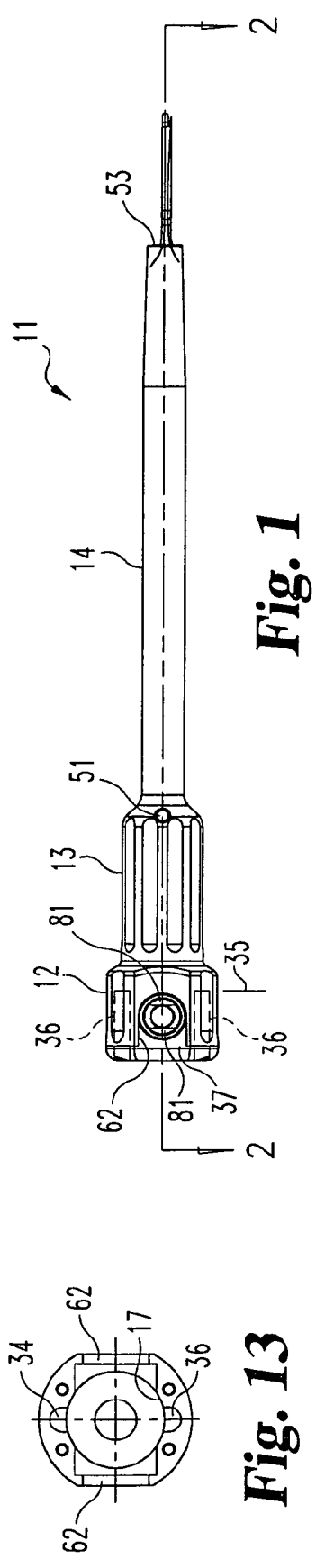
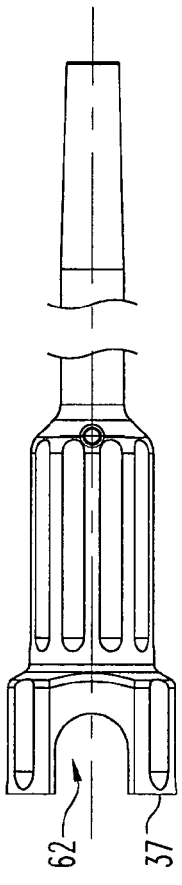
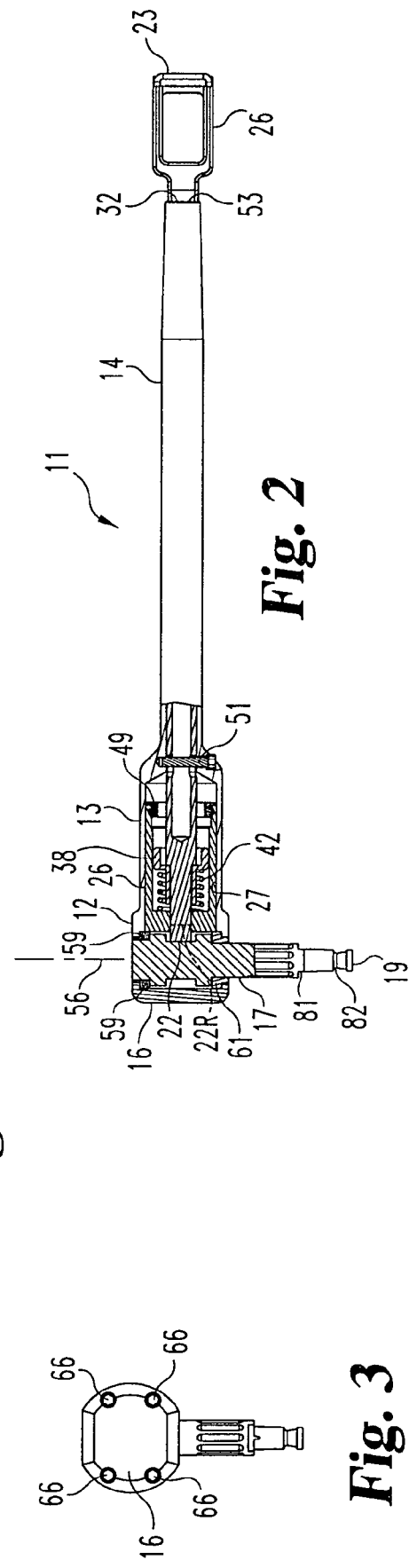

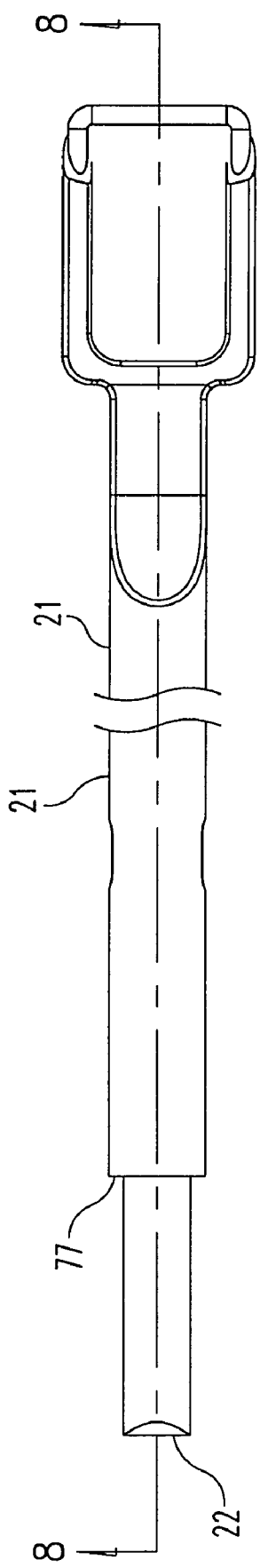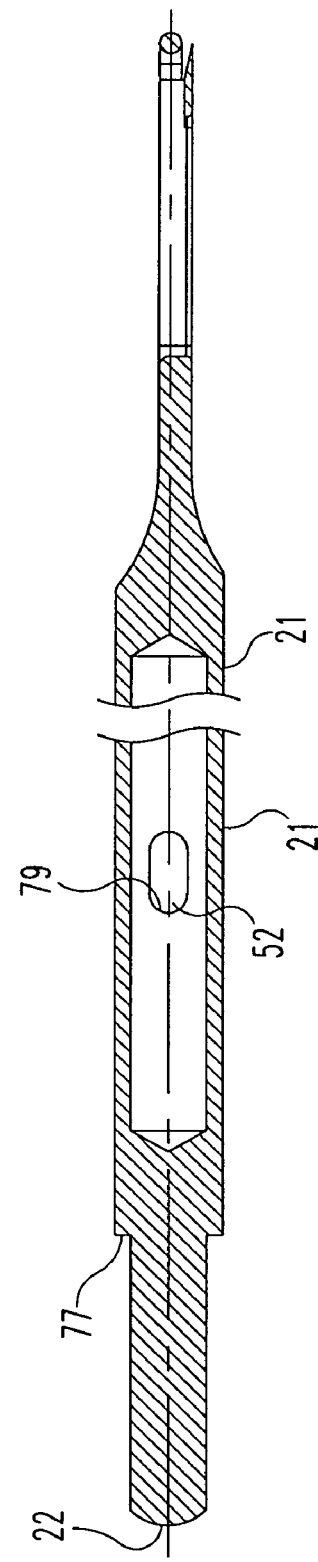
Fig. 7
Fig. 8

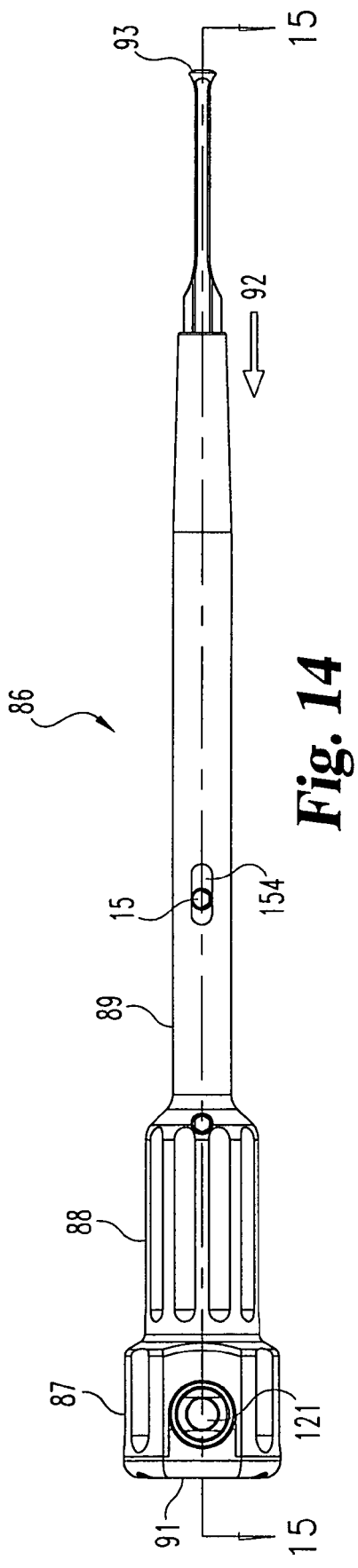
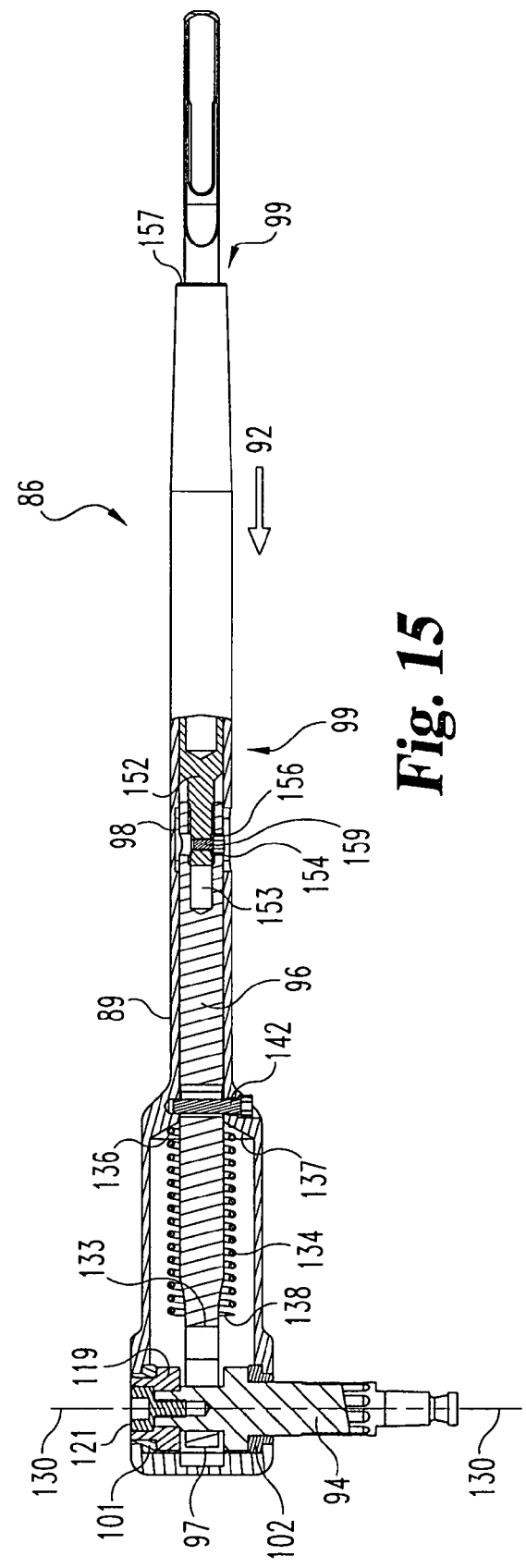

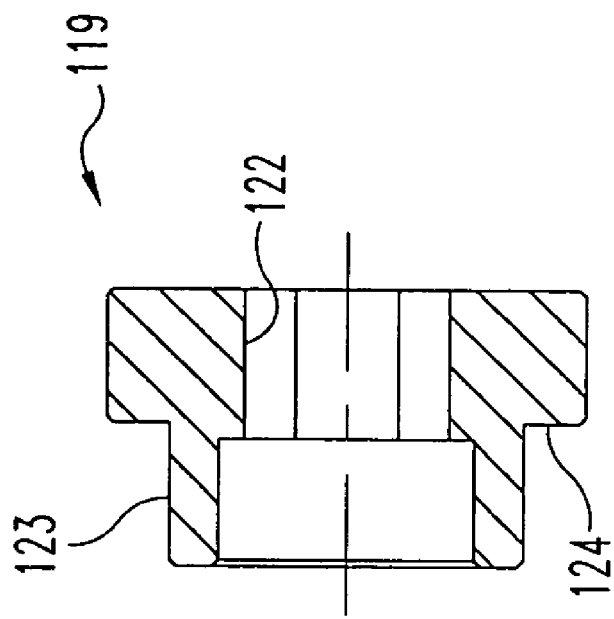
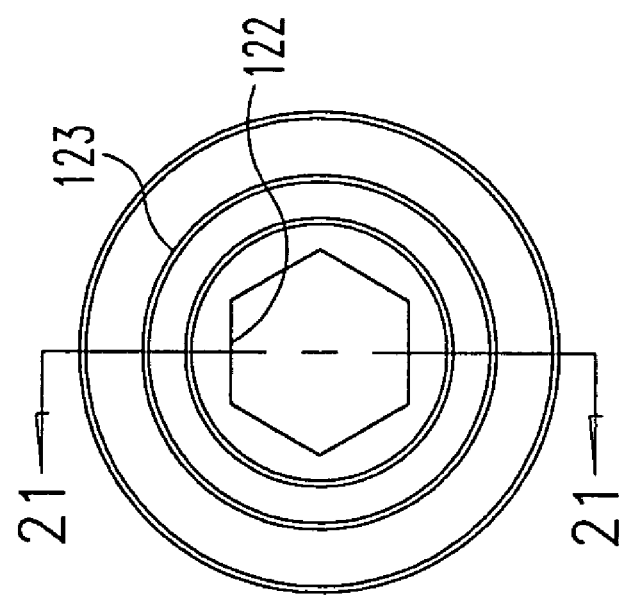
*Fig. 21*
*Fig. 20*

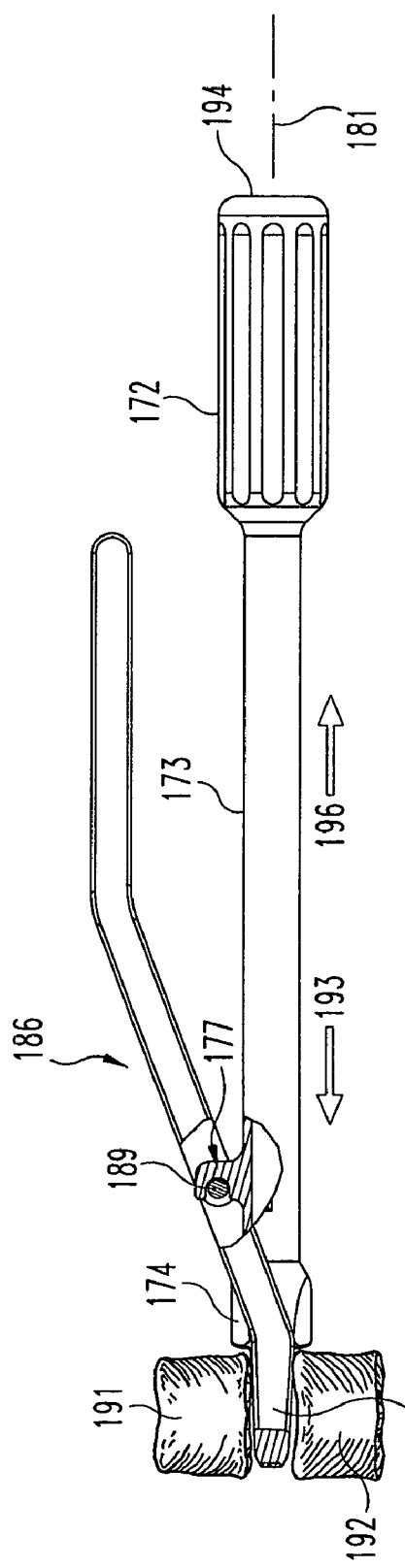
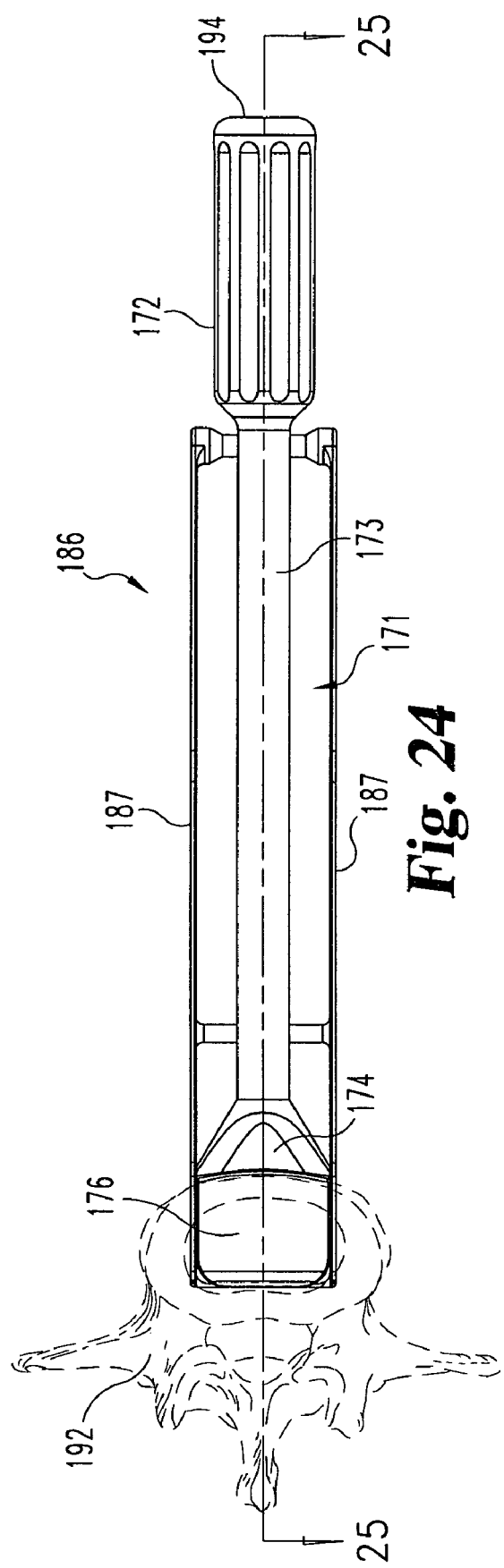
Fig. 25
Fig. 24

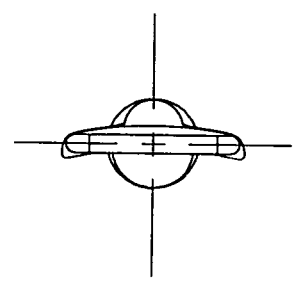
Fig. 38
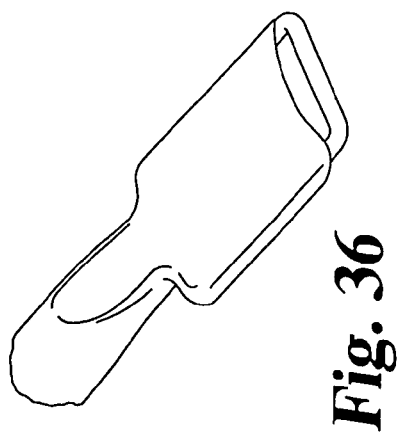
Fig. 36
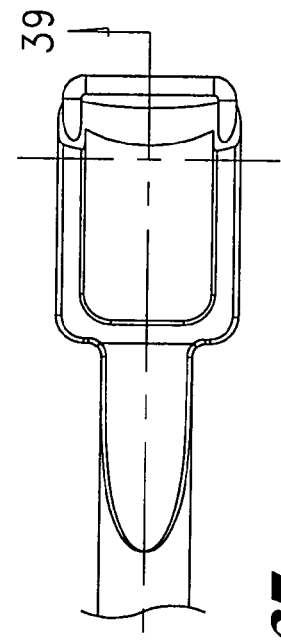
Fig. 37
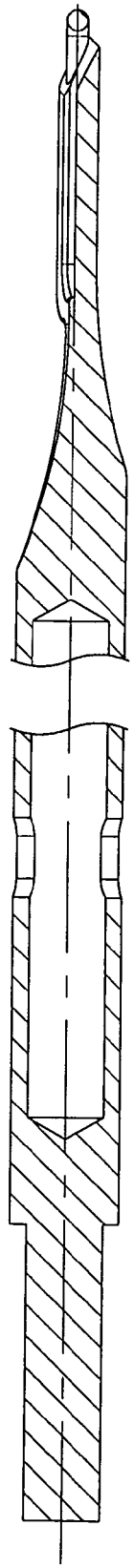
Fig. 39
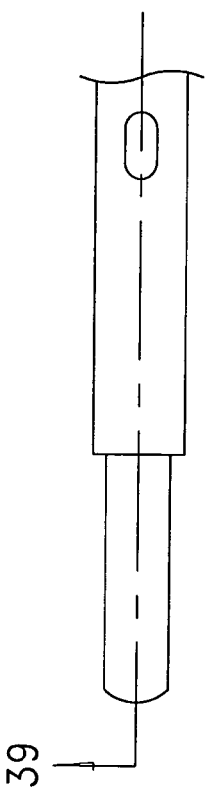
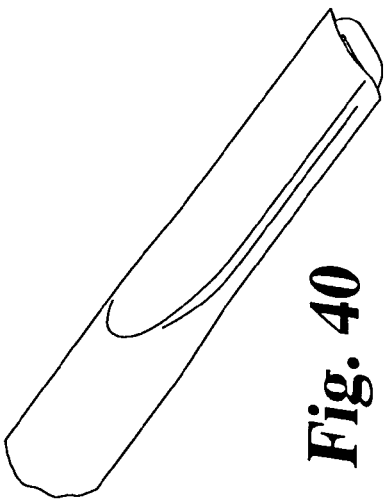
Fig. 40

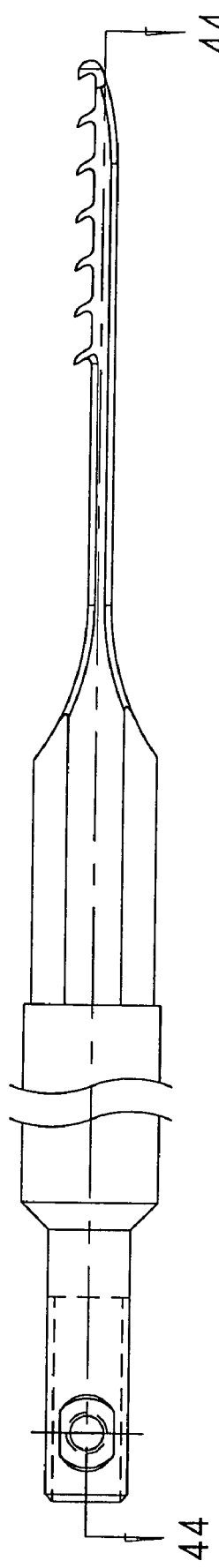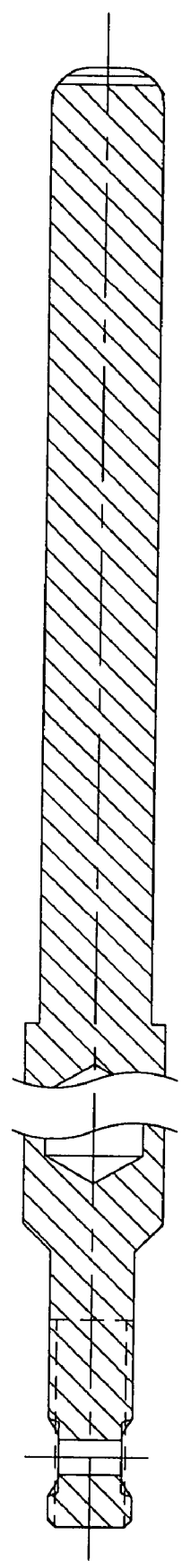
Fig. 43
Fig. 44

IMPULSIVE PERCUSSION INSTRUMENTS FOR ENDPLATE PREPARATION

CROSS REFERENCE TO RELATED APPLICATIONS

The present Application claims foreign priority benefits of European Patent Application Number 03292241.1, filed Sep. 11, 2003, the contents of which are hereby incorporated by reference.

BACKGROUND

This invention relates generally to surgery tools and more particularly to power cutting instruments for vertebral endplate preparation in spinal surgery.

Following removal of some disc materials during spinal surgery, it is important to prepare the endplates of the vertebral bodies for reception of inter-body implant materials. It is desirable to provide devices and procedures for safer, more controlled and more efficient disc space cleaning and endplate preparation. The present invention is directed to providing an additional option for surgeons for improvement in these regards.

SUMMARY

In general, the present invention provides power-operated, hand-held instruments adapted to reception of different types of tissue treatment tools, and drives them in a reciprocating motion.

Further, the invention provides for conversion from a rotary input power source to a reciprocating source, and percussion action in the forward direction in one embodiment, and percussion action in the reverse direction in another embodiment. More specifically, in one embodiment the invention enables use with treatment tools expected to perform more effectively during a forward motion and, in another embodiment, the invention enables use with treatment tools expected to perform more effectively during a reverse motion. Such tools have preferred performance directions, forward or reverse. The invention further comprises treatment tool configurations particularly suitable to the direction and type of cutting action sought. For tools that perform well in either direction, either of the embodiments of the invention may be used. The invention further provides a distractor and keeper arrangement for maintaining distracted disc space height during endplate preparation, the keeper being shaped for convenient use with the powered instruments according to the present invention.

BRIEF DESCRIPTION OF THE FIGURES

FIG. 1 is an elevation view of a percussion instrument according to one embodiment of the present invention.

FIG. 2 is a partial section through it taken at line 2-2 in FIG. 1 and viewed in the direction of the arrows.

FIG. 3 is a left-hand end view thereof.

FIG. 7 is an enlarged elevation view of one type of cutter-shaft combination of the embodiment of FIGS. 1 and 2 but on a larger scale, and with a portion broken out to conserve space in the drawing.

FIG. 8 is a section taken at line 8-8 in FIG. 7 and viewed in the direction of the arrows.

FIG. 12 is a fragmentary elevation view of the proximal end portion of the instrument body of FIG. 1 but on a larger scale and without the end cap and internal parts.

FIG. 13 is a left-hand end view thereof.

FIG. 14 is an elevation view of a second embodiment of the present invention featuring reversed percussion movements (pull back impacts).

FIG. 15 is a view, partially in section taken at line 15-15 in FIG. 14, and viewed in the direction of the arrows.

FIG. 20 is an axial view of the camshaft end bearing.

FIG. 21 is a cross section at line 21-21 in FIG. 20 and viewed in the direction of the arrows.

FIG. 24 is a top (overhead) view of a combination distractor and distractor blade housing used to establish and maintain the desired disc space during use of the instruments of FIGS. 1-23.

FIG. 25 is a section taken at line 25-25 in FIG. 24 and viewed in the direction of the arrows and showing application into the disc space.

FIG. 36 is a perspective view of another embodiment of cutter useful in the FIG. 1 embodiment of the invention.

FIG. 37 is an enlarged overhead view of the complete cutter and shaft for the cutter of FIG. 36 with a portion broken away to conserve space in the drawing.

FIG. 38 is an end view thereof.

FIG. 39 is a section therethrough taken at line 39-39 in FIG. 37 and viewed in the direction of the arrows.

FIG. 40 is a perspective view of another cutter useful with the FIG. 1 embodiment of the invention.

FIG. 43 is an elevation view of another embodiment of the cutter and shaft used with the pull-back embodiment of the invention of FIGS. 14 and 15.

FIG. 44 is a section therethrough taken at line 44-44 in FIG. 43 and viewed in the direction of the arrows.

DESCRIPTION OF THE ILLUSTRATED EMBODIMENTS

Figure 1A:
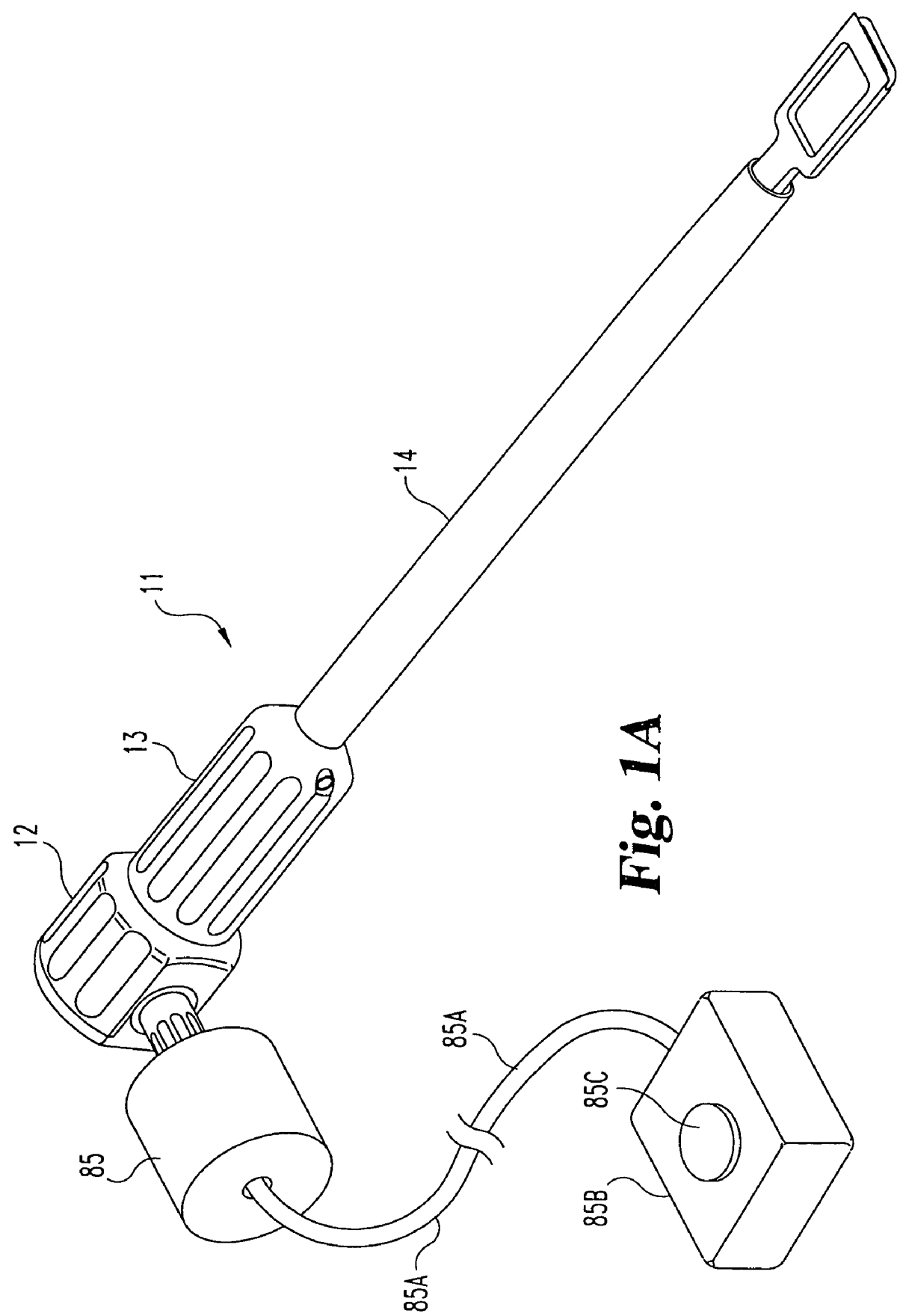
FIG. 1A is a perspective view of the embodiment shown in FIG. 1 and showing, schematically, an example of an air powered rotary motor and air supply line from a foot pedal operated compressor.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Forward Percussion Embodiment

Referring now to the drawings in detail, particularly FIGS. 1-3, 12 and 13, the instrument has a one-piece elongated body 11 having a cam housing portion 12, a spring chamber portion 13, guide barrel portion 14, and end cap 16. A camshaft 17 is received in the cam housing portion.

Figure 10:
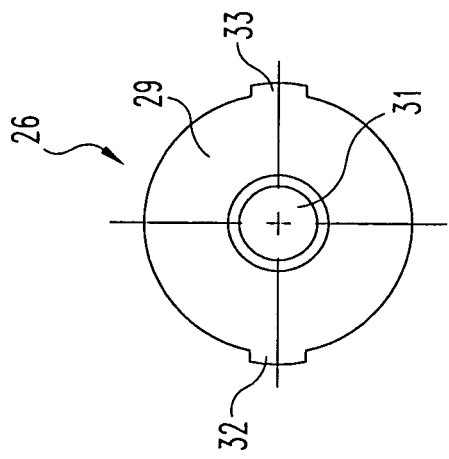
FIG. 10 is a left-hand end view thereof.
Figure 9:
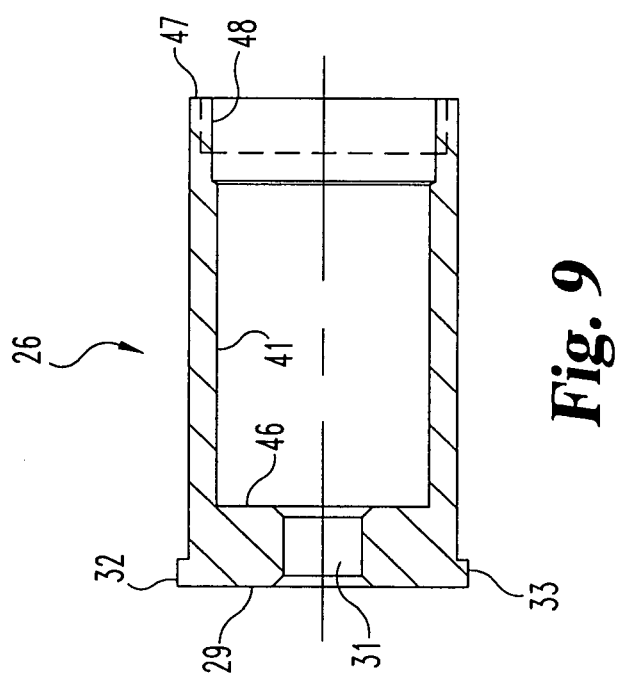
FIG. 9 is an enlarged view of the shaft guide and spring chamber.

A cutter-shaft 21 is received in the guide barrel and has a shaft portion with proximal end 22 and a cutter portion with distal end 23. A spring housing 26 (FIGS. 2, 9 and 10) is received in the bore 27 of the spring chamber portion of the body 11. As best shown in FIGS. 9 and 10, this spring housing has one end wall 29 with a central aperture 31 which receives and guides the proximal end portion of the cutter shaft 21. Housing 26 has stop tabs 32 and 33 at the end wall and which are received in grooves 34 and 36 (FIG. 13, and dashed lines in FIG. 1). These grooves extend longitudinally forward from the proximal end 37 (FIGS. 1 and 12) of the body, and end at plane 35 as shown in FIG. 1. They provide abutments to prevent movement of the housing 26 in the direction of arrow 78, beyond the location shown in FIG. 2. Also, the tabs 32 and 33 in grooves 34 and 36, respectively, prevent rotational movement of the spring housing within the body 11.

The hole 31 in the proximal end wall 29 serves as a proximal end bearing for the cutter shaft 21. Forward portions of the shaft 21 are slidably received and guided by contact of the outer wall of the shaft with the inner wall of the guide barrel portion 14 of the body 11.

Figure 6:
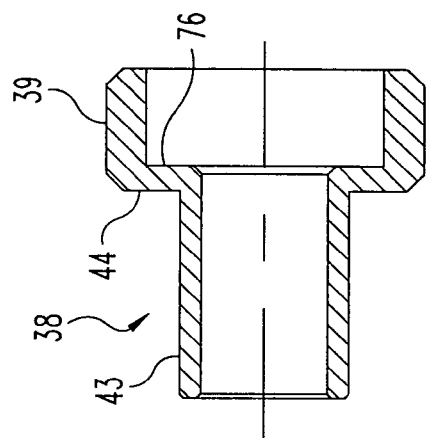
FIG. 6 is an enlarged sectional view of the spring guide and seat member of FIG. 2.

A spring guide and end stop 38 (FIGS. 2 and 6) is slidably received on the proximal end portion of the shaft 21. Its outer rim 39 is slidably received in the bore 41 (FIG. 9) of the housing 26. A coil spring 42 (FIG. 2) is received around the stepped-down portion 43 of the member 38. The shoulder 44 at the step from the cylindrical surface 39 to the cylindrical surface 43 serves as a seat for the distal end of the spring 42. The inside face 46 of the end wall 29 of the housing 26 serves as a spring seat for the proximal end of spring 42.

Figure 11:
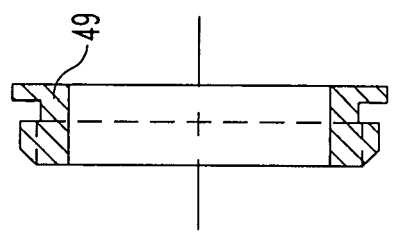
FIG. 11 is a sectional view of the end closure ring for the spring chamber.

The right-hand end portion 47 of housing 26 is internally threaded at 48 and receives end closure ring 49 (FIG. 11) which is screwed into the housing 26. This prevents the member 38 and spring therewith, from sliding out of the assembly when one cutter shaft is removed and replaced by another one having a different type of cutter. Normally, however, a screw 51 (FIGS. 1 and 2) is screwed into the body 11 and extends through an elongated hole 52 in the shaft 21. This screw normally retains the shaft 21 in the body. The length of hole 52 in the axial direction permits a range of shaft reciprocation from engagement with low points on the cam surface to slightly beyond the maximum height of the cam surface. To change cutters, the screw must be removed and then the shaft 21 can be dropped or pulled out from the distal end 53 of the guide barrel 14 followed by installation of the replacement cutter shaft.

Figure 2A:
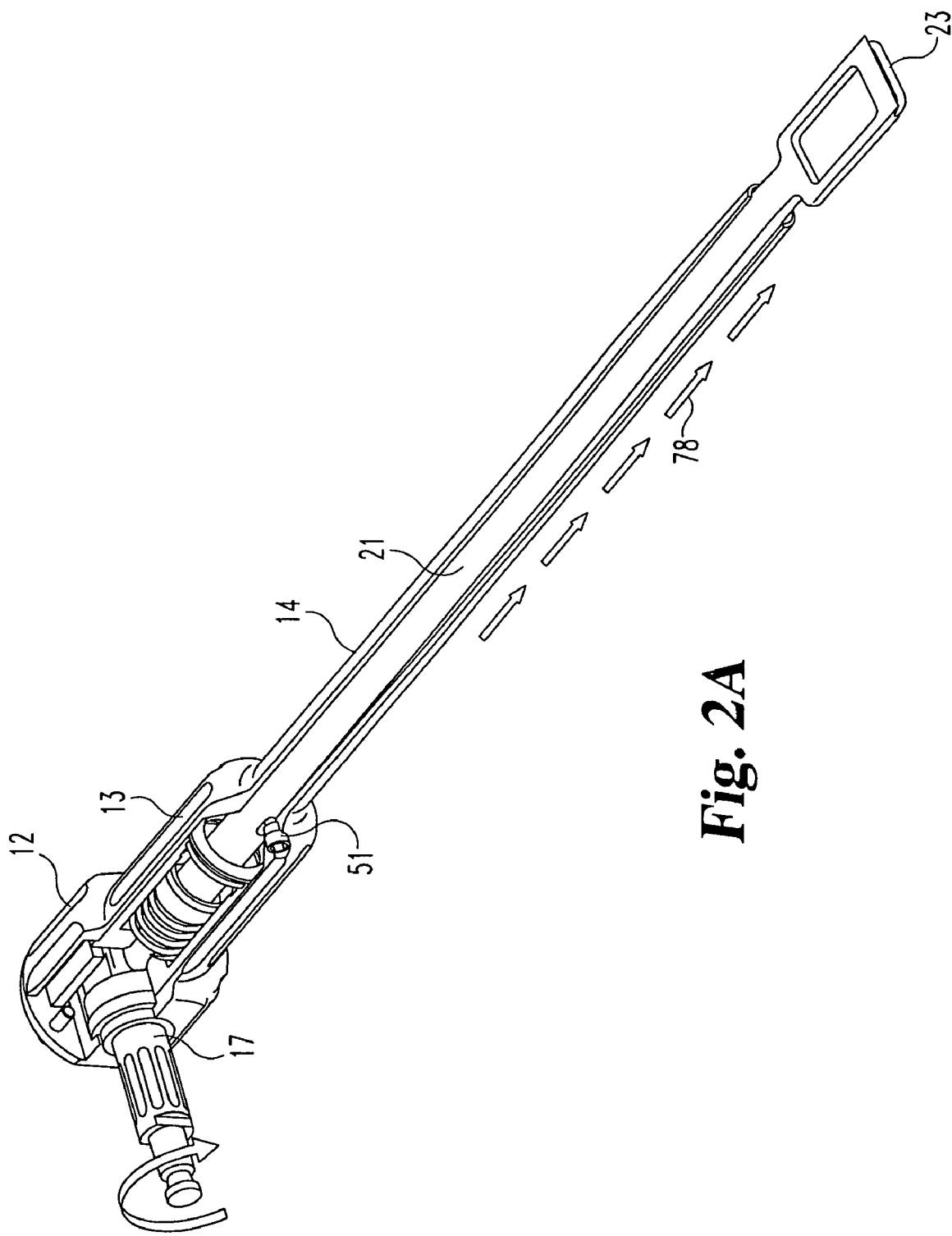
FIG. 2A is a perspective view of the instrument with a quarter section.
Figure 2B:
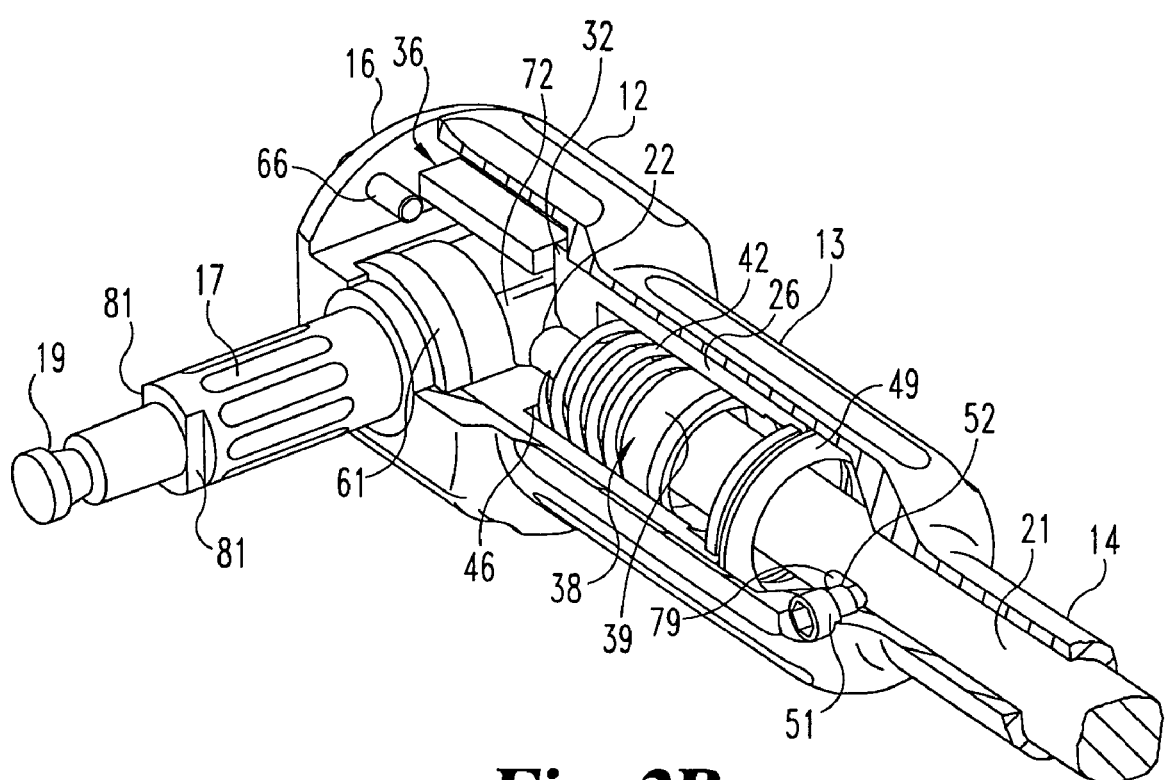
FIG. 2B is an enlarged perspective view of the proximal end portion of FIG. 2.
Figure 5:
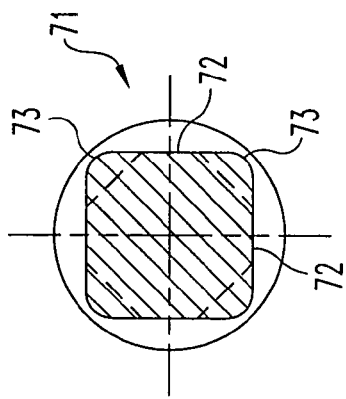
FIG. 5 is a section taken at line 5-5 in FIG. 4 and viewed in the direction of the arrows and showing a square cam cross-section.
Figure 4:
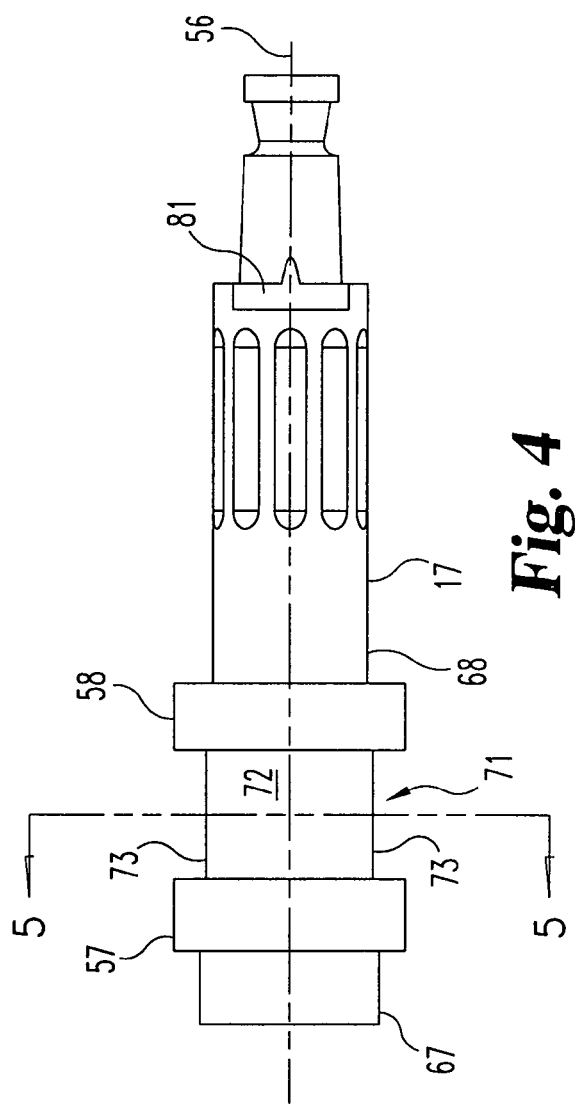
FIG. 4 is an enlarged elevation view of the camshaft thereof.
Figure 23:
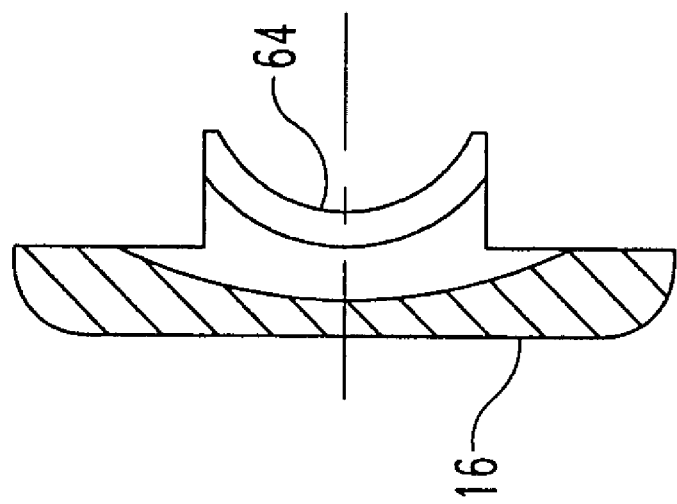
FIG. 23 is a section taken at line 23-23 in FIG. 22 and viewed in the direction of the arrows.
Figure 22:
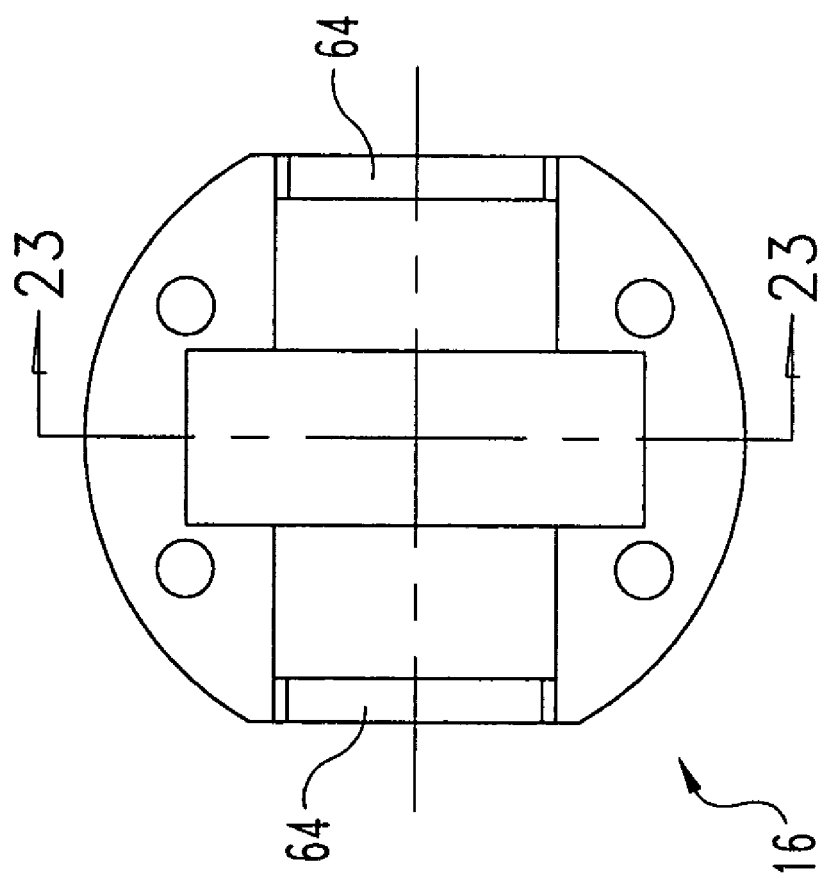
FIG. 22 is an inside face view of the proximal end cap usable in the FIG. 2 and FIG. 15 embodiments of the invention.

Referring now more particularly to FIGS. 4 and 5 along with FIG. 2, the camshaft 17 is generally cylindrical about the axis 56 and has cylindrical flanges 57 and 58 which abut flanged bushings 59 and 61 received in upper and lower, rearwardly opening yokes 62 in the cam housing portion of the body 11 (FIGS. 1 and 12). Similarly, end cap 16 (FIGS. 22 and 23) has yoke portions which receive the bushings 59 and 61 when the end cap is fastened to the body with the four screws 66 (FIG. 3). The bushings 59 and 61 can be engaged by the outboard faces of the flanges 57 and 58 of the camshaft, so they provide location and thrust bearings for the camshaft as well as radial bearings for the smooth cylindrical surfaces 67 and 68 (FIG. 4) of the camshaft. It is seen that the yokes 62 of the body and 64 of the end cap 16, capture the bushings 59 and 61 and thereby capture the cam shaft in the assembly for centering the camshaft axis 56 colinear with the axes of bushings 59 and 61, when the end cap is secured in place by the screws 66.

The cam surface itself shown generally at 71 in FIGS. 4 and 5, is square shaped, having four low areas 72 and four high points 73. Other cam surface profiles may also be used. One example is shown in dotted lines in FIG. 5 in the form of a hexagon. It is the square cam shape which is shown in FIG. 2, with the shaft end 22 (rounded as shown in FIG. 8) engaging a low point on the cam and serving as the cam follower surface. Normally, however, spring 42 urges the spring seat 44 on member 38 (FIG. 6) to the right (in the direction of arrow 78). Abutting engagement of the wall 76 of member 38 with the annular shoulder 77 (FIGS. 7 and 8) of the cutter shaft 21 urges the shaft in the outward direction of arrow 78 (FIG. 2) to an extent limited by the engagement of the proximal end 79 of hole 52 with the stop screw 51. Therefore, in this normal rest position of the cutter shaft, the proximal end 22 thereof will be located, as shown by the dotted line 22R (FIG. 2), spaced away from the circular path of the high points of the cam.

Since this is a power operated instrument, converting rotary motion to reciprocating motion, the cam shaft has flat surfaces 81 for reception of a coupler, and a circular notch 82 for reception of a spring clip or clamp of a coupler from an external rotary power source. This may be any of a variety of power sources such as, electric, hydraulic or more likely an air or nitrogen powered turbine motor 85 (FIG. 1A) coupled to the camshaft. Air may be supplied through tubing 85A from a compressor 85B with speed control pedal 85C. Any other available source of air or other gas with pressure and/or volume control may be used.

Operation—Forward Percussion Embodiment

As an example of the operation of this embodiment of the invention, the user may select the treatment tool to be used, insert it in the barrel 14 and install the screw 51. The tissue treatment tool referred to above and hereinafter is referred to broadly hereinafter as a cutter, and this term is intended to include tools which chisel, file, shape, rasp, polish, broach or otherwise perform the intended effect on or with the body tissue treated.

Before or after installation of the cutter shaft, the user may connect the power source to the camshaft. After positioning the distal end 23 of the cutter at the endplate treatment site and engaging the tissue to be treated, the user may apply force in the forward direction of arrow 78, which is the forward cutting direction of the cutters to be used with this embodiment of the invention. The forward force will compress the spring 42 and move the cam surface toward the shaft end (the cam follower surface) 22. If the camshaft is rotating, percussion action will begin as soon as the shaft end is touched by the high points of the rotating cam, and reciprocating action of the cutter will begin. The speed of such action can be controlled by speed control of the power source, whether by a motor at the instrument (as shown in FIG. 1A), or through a cable or hose and foot control or whatever speed control is desired or available. The percussion impact will depend on how much force the user applies in the direction of arrow 78, as the spring 38 is compressed by increasing force and thereby permits the end of the shaft 22 to project farther into the path of the cam surface as the cam surface moves about the rotational axis 56 of the camshaft.

From the foregoing discussion, it can be recognized that cutter shafts other than shaft 21 shown specifically in FIGS. 1, 2, 7 and 8, may be used in the practice of the present invention. Examples are different types of chisels, shavers and rasps to decorticate the endplate from the disc materials and the cartilage layer. Some are shown in FIGS. 34, 35, 36-39, 40 and 41. It is only necessary to remove the screw 51 and drop or pull cutter shaft 21, select a cutter shaft having a different distal end cutter (the shaft portion from the cutter to the proximal end 22 being of the same configuration as shown in FIGS. 7 and 8), and insert the proximal end of the cutter shaft through the distal end of the barrel 14 and through the bore and spring seat member 38 and into the bore 31 of the housing 26. Of course, it is preferable to have the power source turned off or disconnected from the camshaft during the cutter shaft installation to avoid the risk of having the proximal end 22 struck by the cam and driving the tool back out of the barrel before the limit screw has been installed. Such event might otherwise occur, depending upon whether the cutter shaft is pushed in with enough force to compress the spring 42.

Reverse Percussion Embodiment

This embodiment is discussed with reference to FIGS. 14 through 23, although it will be seen that several of the components described above with reference to the first (forward percussion) embodiment also are used in the reversed percussion embodiment. In this second embodiment of the invention illustrated in FIGS. 14 through 23, some of the components are very similar to those in the first described embodiment. For example, the body 86 has a cam housing portion 87, a spring housing 88 and a guide barrel portion 89. The body 86 is very similar to the body 11 of the first embodiment, and the end cap 91 is virtually identical to the end cap 16 of the first embodiment.

Referring particularly to FIGS. 14-23, and in contrast to the direction of percussion impulse from the cam in the first embodiment, the direction of impulse from the cam in this second embodiment is in the reverse direction so that it pulls the cutter edge 93 in the rearward direction of arrow 92. For that purpose, there is a cam shaft 94 mounted for rotation in the cam housing portion 87 of the body. It operates a cutter drive shaft 96 slidably received in the guide barrel portion 89. Its proximal end portion 97 is associated with the camshaft, while its distal end portion 98 receives a proximal end portion 99 of a cutter shaft having the cutter 93 at its distal end.

Figure 17:
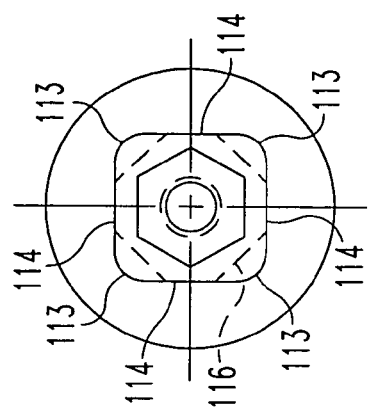
FIG. 17 is an end view of the camshaft.
Figure 16:
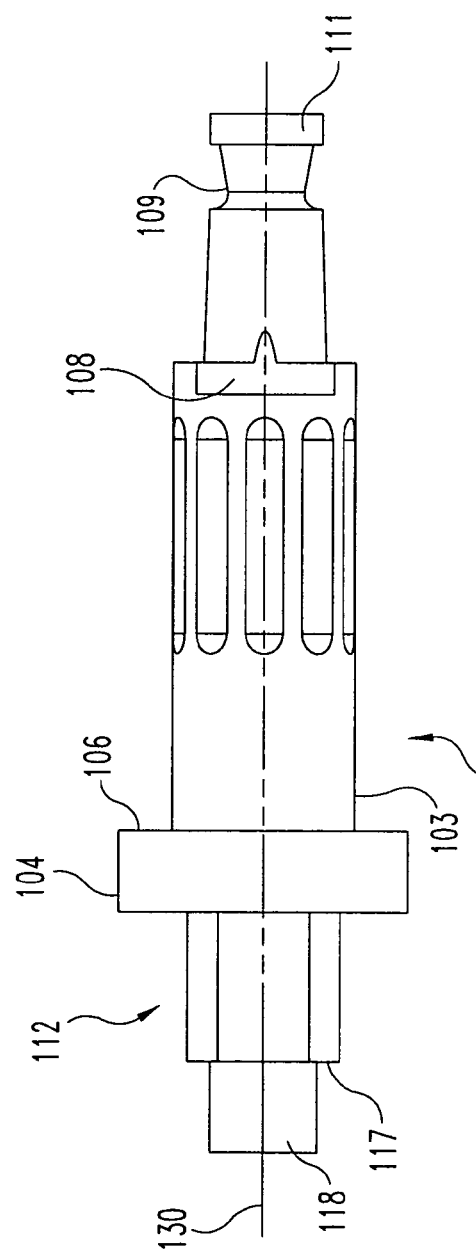
FIG. 16 is an enlarged elevation view of the camshaft.

Referring now to FIGS. 16 and 17 along with FIG. 15, the camshaft 74 is mounted in the body in bushings 101 and 102 which are received and located in the housing in essentially the same way as are bushings 59 and 61 described above with reference to the first embodiment. The camshaft itself has a smooth cylindrical surface at 103 receiving radial bearing support by bushing 102. It also has a cylindrical flange 104 having outer face 106 engaging bushing 102 for thrust bearing support. The outer end portion of the camshaft has a pair of diametrically opposed flat surfaces 108 on the otherwise cylindrical surface 103 which provide anti-rotation cooperation with a connector of a rotary power source in the same manner as for the first described embodiment. Likewise, it has a stem with annular groove 109 and head 111 to cooperate with the power source connector and retain it in place. Accordingly, the drive for this camshaft is like that for the first embodiment.

In this embodiment, the cam surface itself is shown at 112 as a square, having four high points 113 and four flat surfaces 114, the center of each flat 114, as in the square cam of the first embodiment, being a low point in the cam travel. The cam can have other cross sectional shapes as mentioned above. One of several possible shapes could be hexagonal as designated by the dash line 116 in FIG. 17. At the end face 117 of the cam 112, there is a step inward to a hexagonal post 118 non-rotatably received in bearing 119 (FIGS. 20 and 21) and secured to the bearing by a socket head screw 121 screwed into the end of the camshaft. The hexagonal post 118 on the camshaft is received in the hexagonal aperture 122 of the bearing 119 which is rotatably received in bushing 101. Thus, the cylindrical surface 123 of the bearing 119 rotating in the bushing 101 provides radial bearing support for the camshaft, and the circular face 124 of the bearing 119 slidingly engaging the lower face of bushing 101 provides thrust bearing support for the camshaft.

Figure 18:
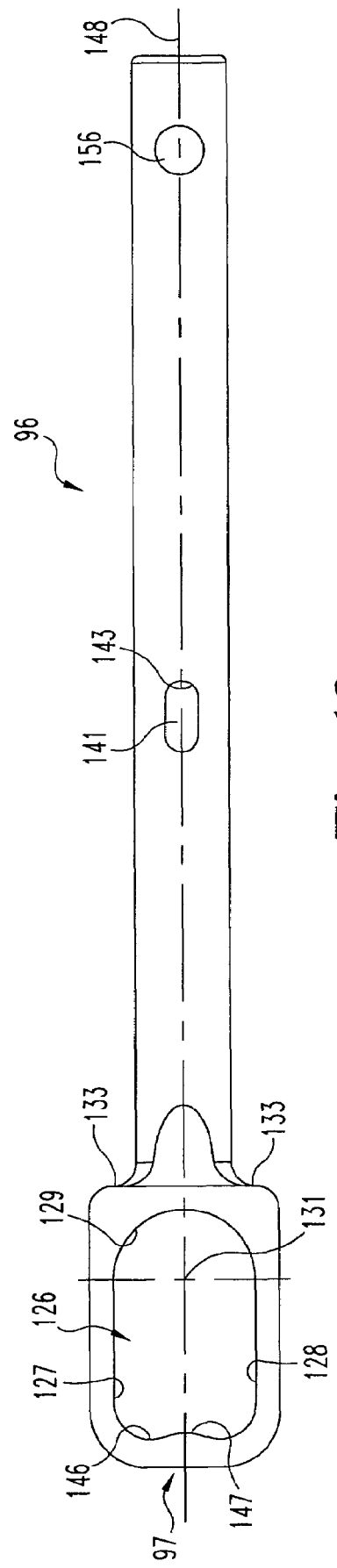
FIG. 18 is a top (overhead) view of the cutter drive shaft.
Figure 19:
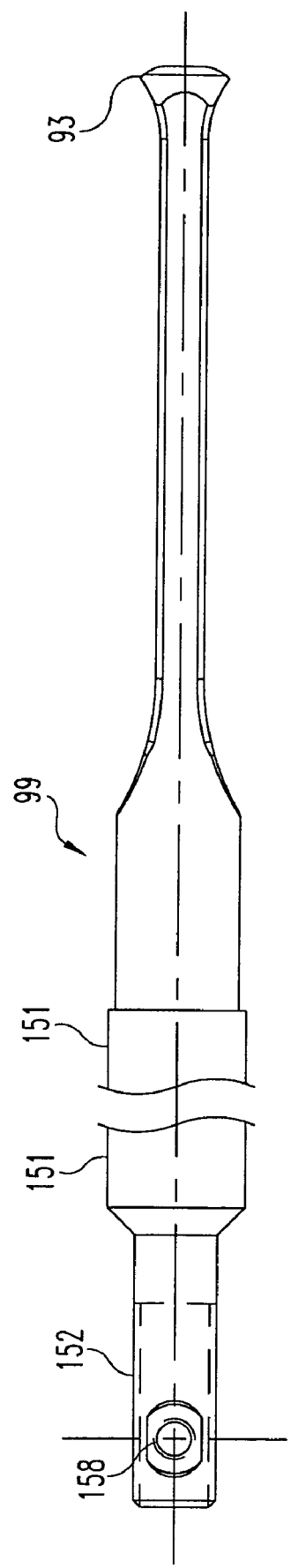
FIG. 19 is a view of the version of reversed percussion cutter shaft as shown in FIGS. 14 and 15, but with a portion of the length thereof broken away to conserve space in the drawing.

Referring now particularly to FIGS. 15 and 18, the cutter drive shaft 96 for the cutter shaft has a cam follower end portion 97 configured for following the cam 112. It is illustrated in the form of an elongate hole 126 with straight parallel sidewalls 127 and 128 and a semi-circular end wall 129 having a radius equal to half the distance between the sidewalls 127 and 128 and centered at 131. This radius is slightly greater than the distance diametrically across the high points 113 of the cam and is centered on the cam axis 130. The follower end portion 97 framing the hole 126 has a shoulder 133. A spring 134 (FIG. 15) is a compression spring having a right-hand end 136 bearing on wall 137 of the spring chamber portion of the body 86. The left-hand end of the spring abuttingly engages the shoulder 133 of the follower end portion of the shaft 96. Therefore, the spring normally pushes the shaft 96 to the left in the direction of arrow 92.

An elongate hole 141 through shaft 96 receives travel limit screw 142, which is screwed into the instrument body 86.

When the instrument is idle, the spring 134 moves the drive shaft 96 to the left until the right-hand end 143 of the hole 141 engages and is stopped by the screw 142. This is the normal rest position of the shaft and places it such that the center 131 of the curved surface 129 of the cam shaft frame hole 126 is spaced slightly outboard of the circle defined by the four high points of the cam when the camshaft is rotated.

The left-hand end wall 146 of the cam follower portion 97 is provided with extra thickness resulting in a bulge 147 at the longitudinal axis 148 of the cutter drive shaft 96 and serves as the cam follower surface of cutter drive shaft 96.

Figure 42:
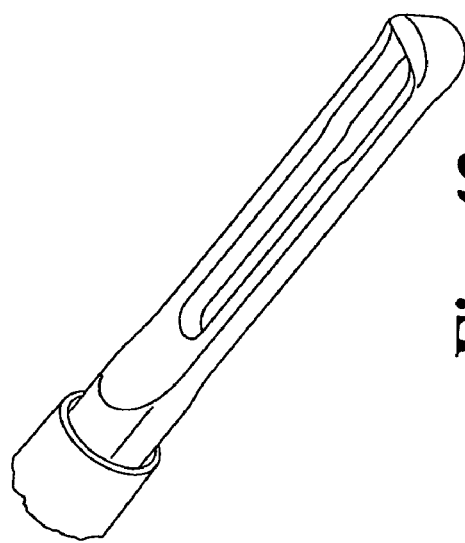
FIG. 42 is a perspective view of the cutter shown in the illustrations of FIGS. 14, 15 and 19 for the pull-back embodiment of the invention.

This embodiment of the invention can be provided with a variety of cutters of various configurations and types useful, particularly when pulled toward the surgeon. Some examples are different types of curettes, scrapers and pull shavers. One example is the cutter shaft 99 shown in elevation view in FIG. 19 and partially shown in FIGS. 14 and 42 and shown partially in section in FIG. 15. This cutter shaft 99 has a cylindrical body portion 151 slidably received on the inside bore of the barrel 89 of the instrument. A stem portion 152 of the tool has less diameter than the body portion 151 and is slidably received in a bore 153 in the distal end portion of the cutter drive shaft 96. The barrel 89 of the instrument has an elongate hole 154 at one location in the wall. A hole 156 (FIG. 18) in cutter drive shaft 96 is normally aligned or in registry with the hole 154 in the housing when the cutter drive shaft is in rest position dictated by the engagement of the stop screw 142 with the end wall 143 of hole 141 in the cutter drive shaft. This is under the urging of the spring 134. So when the cutter shaft is installed in the direction of arrow 92 into the open end 157 of the instrument body, it can be advanced to the left so that the cutter stem 152 received in bore 153 has the threaded hole 158 of the cutter stem 152 located in registry or lined up with the hole 156 in the cutter drive shaft 96. Then screw 159 can be inserted through the hole 154 in the guide barrel 89 and screwed into the cutter shaft hole 158 to fasten the cutter shaft 99 to the cutter drive shaft 96. The screw head is stopped so that it resides in the hole 156 in the cutter drive shaft, retaining the cutter shaft in place but recessed slightly from the inside wall of the barrel 89 to avoid interference with reciprocation of the cutter shaft. Besides, the hole 154 in the wall 89 is long enough that the screw can move forward and backward in the direction of arrow 92 within the hole 154 during reciprocation of the drive shaft 96. With this arrangement, the cutter shaft 99 can be readily removed from the guide barrel by simply removing screw 159 and pulling the cutter shaft out of the barrel. Another cutter shaft with a different configuration of the cutter portion but with the same configuration otherwise, can then be inserted through the end 157 in the direction of arrow 92. When the anchor hole 158 thereof is lined up with the hole 154, the screw 159 is installed to fix the new cutter shaft to the drive shaft 96 in preparation for using the new cutter.

Operation—Reverse Percussion Embodiment

As mentioned above, the surgeon can run the cam constantly if desired, or can start it and stop it at the beginning and end of a cutting operation. Depending upon the power source available, the speed of rotation may be varied and thus, the speed of the cutter strokes would vary. A reciprocating action begins when the surgeon has engaged the cutter with the surface to be treated and pulls the instrument in the direction of arrow 92 with the cutter edge 93 engaging the surface to be prepared. The force of impact between the cutter edge 93 and material to be cut, is determined largely by the force with which the instrument is pulled in the direction of arrow 92, which thereby compresses the spring 134 and enables the cam engaging follower surface 147 of the cam follower to impinge on the path of rotation of the high points of the cam. The rate of impulses depends upon the speed of the camshaft as determined by the surgeon.

Figure 35:
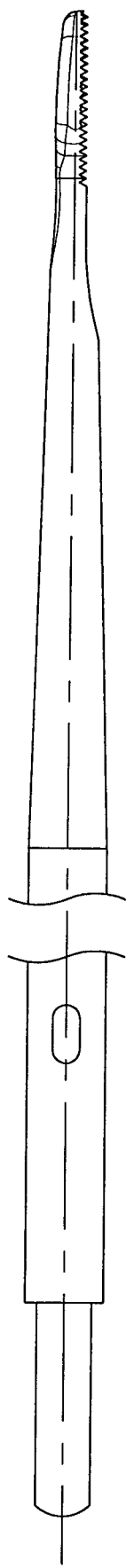
FIG. 35 is an elevation view of the cutter and shaft for the cutter of FIG. 34, with a portion broken away to conserve space in the drawing.
Figure 34:
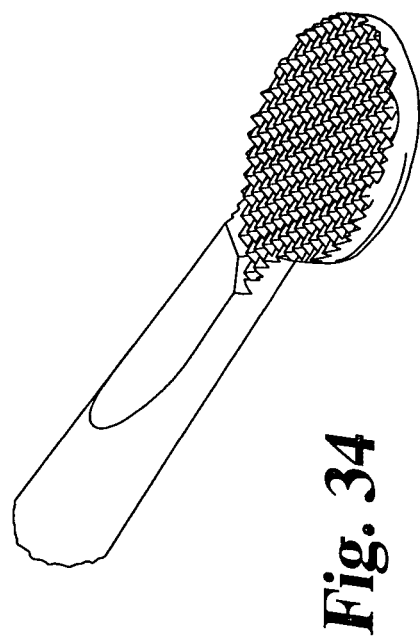
FIG. 34 is a perspective view of another type of cutter.
Figure 41:
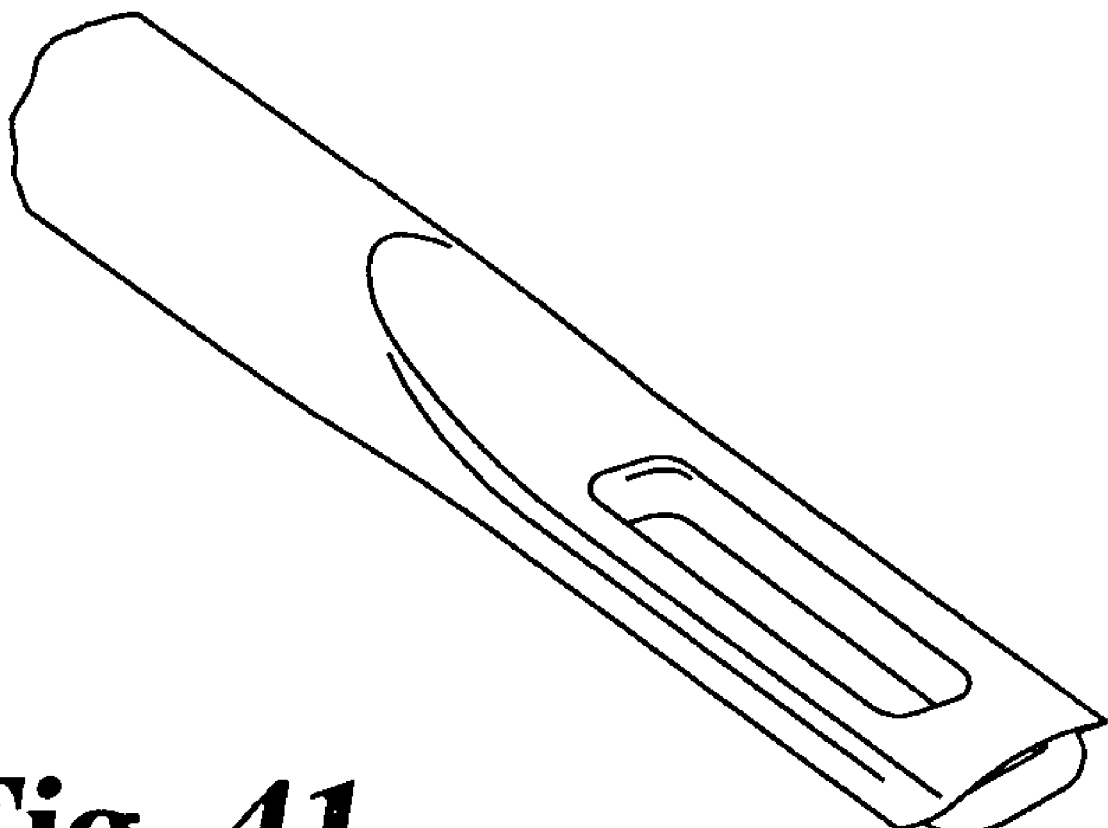
FIG. 41 is a perspective view of still another cutter similar to that of FIG. 33 but narrower.

It can be understood that some cutters may be useful and which can treat the tissue in a useful way regardless of whether the cutter is driven in the forward or reverse direction. Such cutters can be used in either the forward or reverse percussion type instrument described above, if the proximal end portion of the cutter shaft is shaped and located to work with the cam and follower arrangement provided in the instrument. One example is a cutter as shown in FIGS. 34 and 35. With the shaft as shown in those figures, the cutter will work with the forward percussion instrument. If the shaft is made as shown in FIGS. 43 and 44, the cutter will work with the reverse percussion instrument.

Disc Height Maintenance

Figure 26:
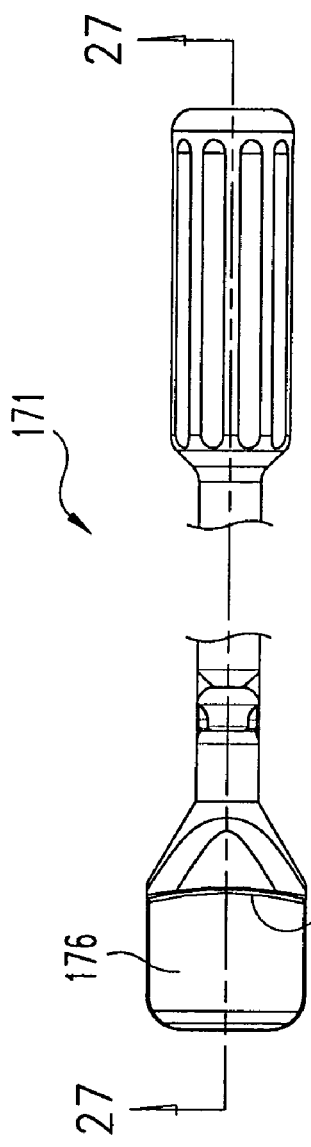
FIG. 26 is a top (overhead) view of the distractor itself with a portion broken away from the middle to conserve space in the drawing.
Figure 27:
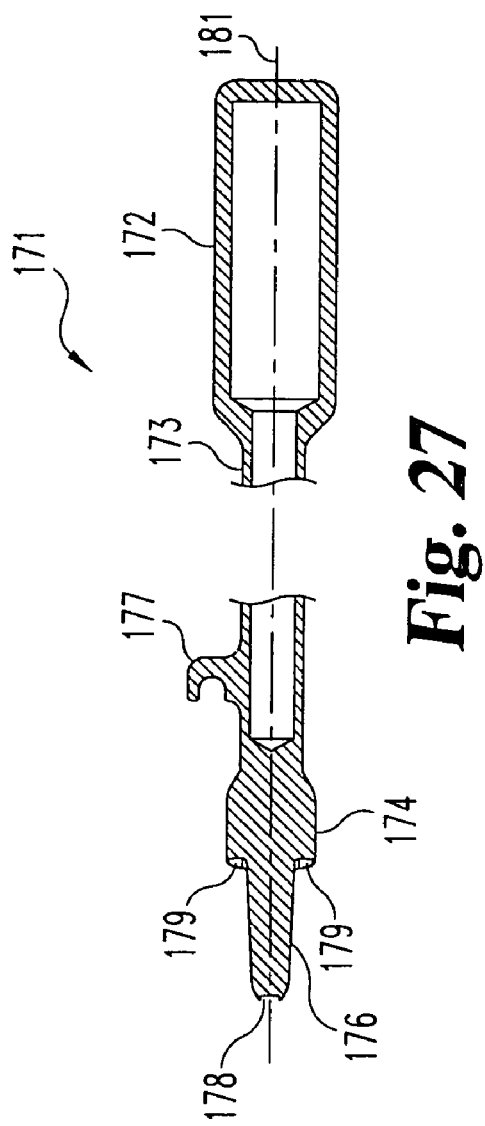
FIG. 27 is a section taken at line 27-27 in FIG. 26 and viewed in the direction of the arrows.
Figure 28:
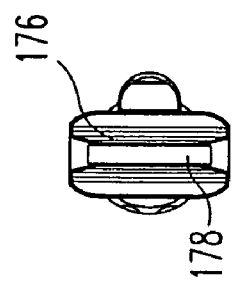
FIG. 28 is a left-hand end view thereof.
Figure 32:
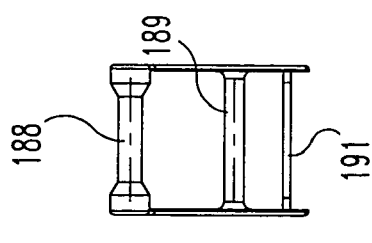
FIG. 32 is a right-hand view thereof.
Figure 30:
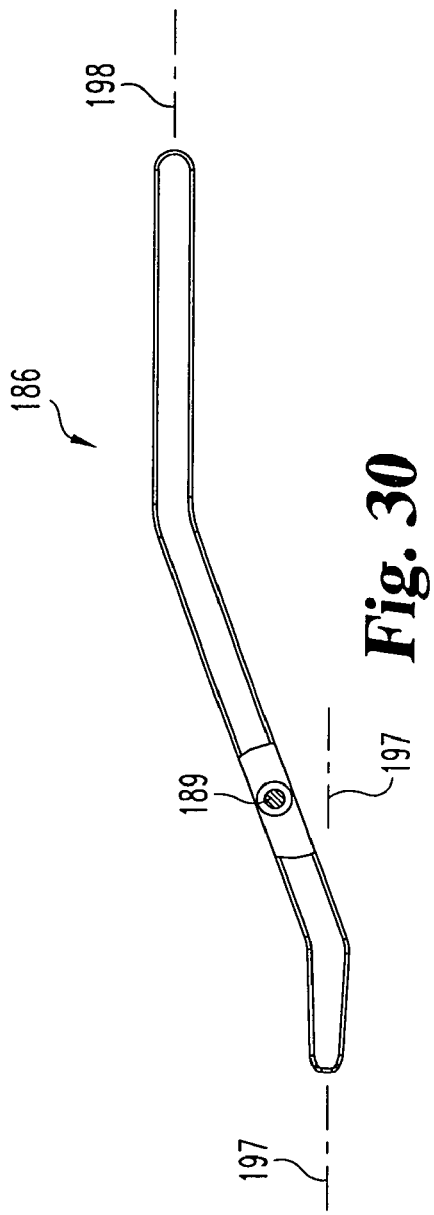
FIG. 30 is a section view taken at line 30-30 in FIG. 29 and viewed in the direction of the arrows.
Figure 31:
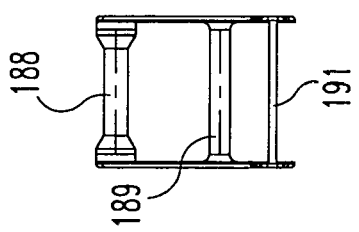
FIG. 31 is a left-hand view thereof.
Figure 29:
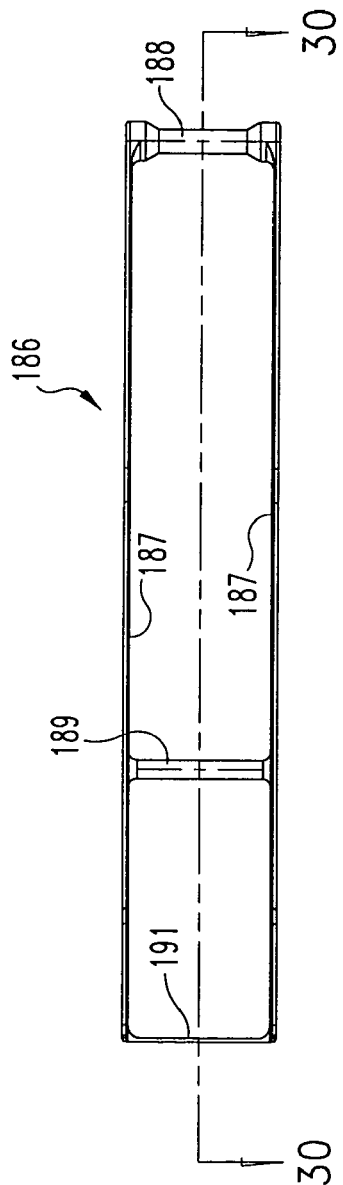
FIG. 29 is a top (overhead) view of the distractor blade housing which serves also as the disc space keeper.
Figure 33:
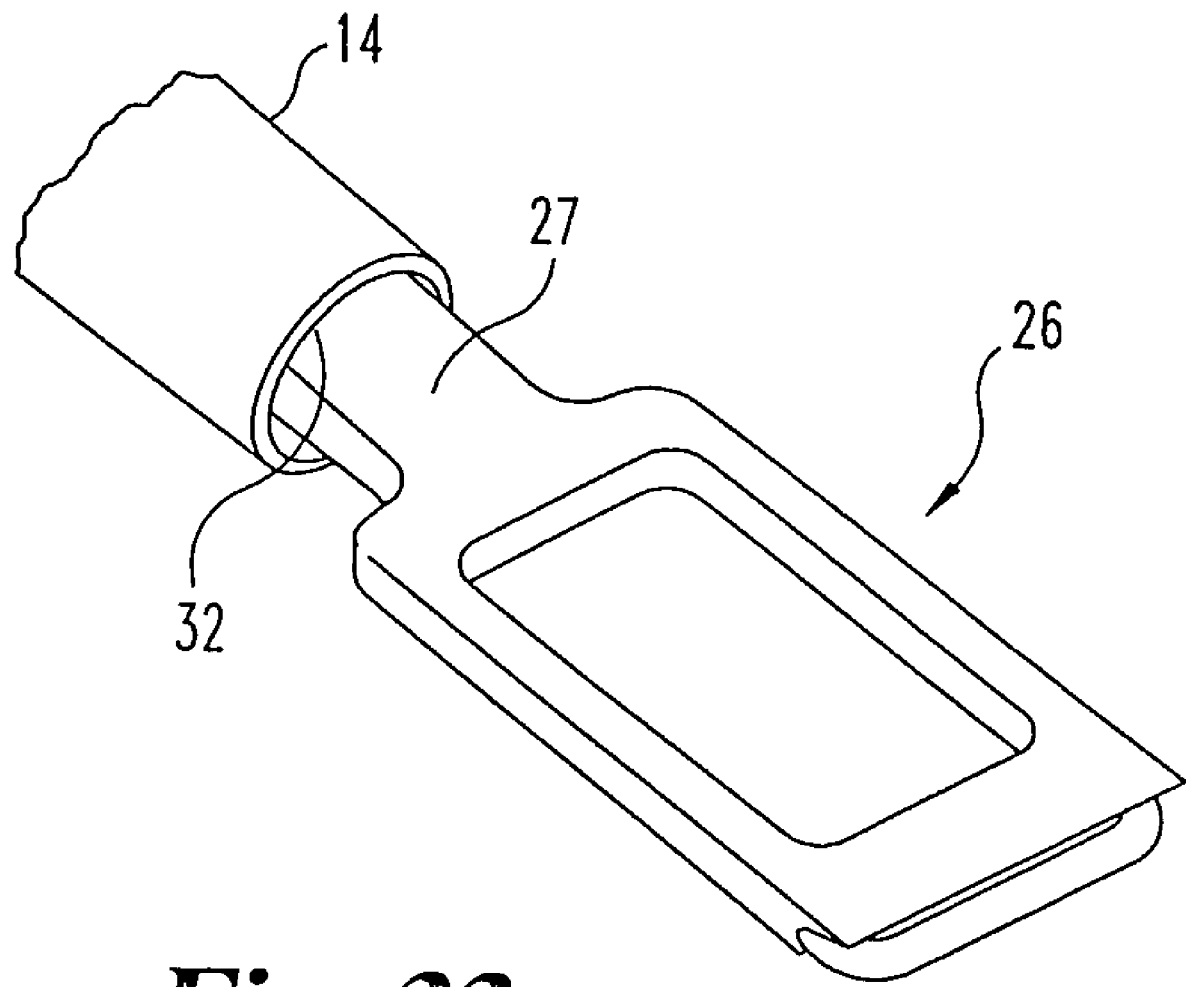
FIG. 33 is an enlarged perspective view of the cutter illustrated in the FIGS. 1, 2, 7 and 8 illustrations.

Referring now to FIGS. 24-30, there is shown apparatus used according to the present invention to facilitate use of either of the two previously described embodiments. Referring first to FIGS. 24 and 25, a combination distractor and disc space keeper is shown. As shown specifically in FIGS. 26-28, the illustrated distractor 171 includes a handle portion 172, shaft portion 173, head portion 174, and wedge portion 176. A forwardly opening hook 177 is fixed atop the shaft portion near the head portion. The wedge portion has a transverse groove 178 at the tip. Abutments 179 are provided at the transition from tip portion to head portion and are slightly arcuate in shape, as shown in FIG. 26. The upper and lower surfaces of the tip portion converge at a five degree total angle, half above and half below a plane containing the axis 181 of the shaft and handle portions. Referring particularly to FIGS. 29-32, a distractor blade housing 186 and which serves as the disc space keeper, is made in the form of a frame and includes parallel side members 187, a rear cross member 188, an intermediate cross member 189 serving as a hinge pin, and a front cross member 191.

In the use of this device, and after the removal of the disc from the space between vertebral bodies shown schematically at 191 and 192 in FIGS. 24 and 25, the distractor 171 is assembled with the blade housing 186 by inserting the wedge portion between the housing side members and moving it forward to engagement of the groove 178 of the distractor tip with the front cross member 191 of the blade housing and simultaneously receiving the hinge pin 189 in the hook 177, as shown in FIG. 25. Then, approaching from the anterior side of the spine, the space from which the disc material has been previously removed is approached in the direction of the arrow 193, and the handle 172 is pushed in that direction to open up the space to approximately eight or ten millimeters, or to such other extent as desired, and by hammer or other impulses on the handle end 194, if needed. After the desired disc height is established in this manner, the distractor handle is pulled out in the direction of arrow 196, while the blade housing 186 remains in place and maintains the disc height as desired, thus serving as the disc space keeper. Because of the offset between the plane 197 (FIG. 30) containing the frame cross member 191, and the parallel plane 198 containing the axis of the rear cross member 188, there is ample room for entry and manipulation of a cutter in the space between the vertebral bodies and entry of the percussion instrument in the space between the plane 197 and the pivot pin 189 and rear cross member 188 of the keeper frame.

While the views in FIGS. 24 and 25 show the combination with the hook 177 of the distractor and the rear cross member 188 of the keeper above the axis 181 of the distractor, the assembly can be used with the orientation inverted relative to that shown in FIG. 25. As with the cutting instruments themselves, the orientation will depend upon the preferences of the surgeon.

The preferred material for the larger components is stainless steel; however, the used of other materials suitable for the intended functions are also contemplated as falling within the scope of the invention.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A powered, hand-held instrument for treating vertebral endplates, comprising:
   a body configured to be held in a surgeon's hand;
   a camshaft rotatable about a rotational axis in said body and having a cam surface rotatable about said rotational axis;
   a cutter shaft having a proximal end and a distal end, said cutter shaft extending along a longitudinal axis and being mounted in said body to reciprocate in forward and reverse directions along said longitudinal axis;
   a cutter disposed at said distal end of said cutter shaft and configured to have a preferred performance direction in one of said forward and reverse directions;
   said cutter shaft being moveable in said preferred performance direction by said cam surface when said camshaft is rotating;
   a cutter drive shaft having a proximal end and a distal end, said cutter drive shaft having a first connector at said distal end and a cam follower surface adjacent said proximal end and facing said cam surface;
   said cutter engaged to said cutter shaft and having a reverse preferred performance direction, said cutter shaft having a second connector at said proximal end of said cutter shaft, said second connector connected to the first connector to transmit axial force between said cutter drive shaft and said cutter shaft; and
   means for normally disabling movement of said cutter shaft by said camshaft, said means for disabling being a compression spring bearing on said body and on a portion of said cutter drive shaft to urge said cam follower surface in a reverse direction away from said cam surface.

2. The instrument of claim 1 and wherein:
   said proximal end portion of said cutter drive shaft includes a ring portion encircling said camshaft and having said cam follower surface facing an inner surface of said ring.

3. The instrument of claim 2 and wherein:
   said ring portion has a spring seat shoulder thereon; and
   said spring bearing on said spring seat shoulder to urge said cutter drive shaft in a reverse direction to displace said cam follower surface away from said cam surface of said camshaft.

4. A powered, hand-held instrument for treating vertebral endplates, comprising:
   a body configured to be held in a surgeon's hand;
   a camshaft rotatable about a rotational axis in said body and having a cam surface rotatable about said rotational axis;
   a cutter shaft having a proximal end and a distal end, said cutter shaft extending along a longitudinal axis and being mounted in said body to reciprocate in forward and reverse directions along said longitudinal axis;
   a screw secured in said body and oriented transverse to said longitudinal axis; and
   an elongate hole in said cutter shaft configured to receive said screw therethrough for limiting said travel of said cutter shaft in both of said forward and reverse directions;
   a cutter disposed at said distal end of said cutter shaft and configured to have a preferred performance direction in one of said forward and reverse directions;
   said cutter shaft being moveable in said preferred performance direction by said cam surface when said camshaft is rotating; and
   means on said body for normally disabling movement of said cutter shaft by said camshaft.

5. The instrument of claim 4 and wherein:
   said means for disabling is arranged to be neutralized by manual force applied to said body in said preferred performance direction.

6. The instrument of claim 4 and wherein:
   said cutter shaft has a cam follower surface facing said cam surface; and
   said means for disabling comprise a compressed spring bearing on said body and on said cutter shaft to urge said cam follower away from said cam surface.

7. The instrument of claim 4 and wherein:
   said means for disabling comprise a resilient member normally urging said cutter shaft in said preferred performance direction.

8. The instrument of claim 7 and wherein:
   said resilient member comprises a compressed coil spring.

9. The instrument of claim 4 and further comprising:
   a cutter drive shaft having a longitudinal axis and having a proximal end and a distal end, said cutter drive shaft having a cam follower surface adjacent said proximal end and facing said cam surface;
   said cutter drive shaft having an elongate hole extending axially rearward from said distal end of said cutter drive shaft;
   said cutter shaft having an elongate stem received in said elongate hole in said cutter drive shaft;
   said cutter drive shaft having a second hole transverse to said cutter drive shaft axis; and
   a second screw extending into said second hole and threadable into said cutter shaft to retain said cutter shaft in said cutter drive shaft.

10. The instrument of claim 9 and wherein:
    said second screw has a head disposed in said second hole and abuttingly engageable with a wall of said second hole to limit relative axial movement between said cutter shaft and said cutter drive shaft.

11. The instrument of claim 4 wherein said longitudinal axis is arranged transverse to said rotational axis.

12. An instrument for cutting bodily tissue, comprising:
    an instrument body;
    a camshaft mounted to said body and having a rotary power source input adapter for rotation of said camshaft about a rotational axis, said camshaft having a cam surface with locations thereon arranged at different radial distances from said rotational axis;
    a cutter shaft mounted to said body for reciprocation therein, and having a proximal end and a distal end;
    a cutter engaged with said cutter shaft adjacent said distal end; and a cam follower having a cam follower surface operable to displace said cutter when engaged with said cam surface during rotation of said camshaft; and a cutter drive shaft having a proximal end and a distal end, said cutter drive shaft having a first connector at said distal end and defining said cam follower surface adjacent said proximal end and facing said cam surface;

said cutter engaged to said cutter shaft and having a reverse preferred performance direction, said cutter shaft having a second connector at said proximal end of said cutter shaft, said second connector connected to the first connector to transmit axial force between said cutter drive shaft and said cutter shaft; and wherein said cam surface is normally disengaged from said cam follower surface but is operably engagable with said cam follower surface during rotation of said cam shaft for impact driving said cutter in a first direction.

13. The instrument of claim 12 and further comprising:
means for normally disengaging said cam follower surface from said cam surface.

14. The instrument of claim 13 and wherein:
said means for normally disengaging is a spring.

15. The instrument of claim 14 and wherein:
said spring is a return spring effecting return of said cam follower surface opposite said first direction of impact driving said cutter, said spring normally applying a return force to hold said cam follower surface away from said rotating cam surface.

16. The instrument of claim 14 and wherein:
said spring is a compression spring having a proximal end seated in a fixed location in said body, and having a distal end engaging a shoulder on said cutter shaft and urging said cutter shaft in a forward direction.

17. The instrument of claim 14 and wherein:
said spring is a compression spring having a distal end seated at a constant location in said body and having a proximal end engaging a shoulder on said cutter shaft and urging said cutter shaft in a reverse direction to normally maintain said cam follower surface spaced from said cam surface.

18. A powered instrument for surgical use, comprising:
a body having a cam housing portion and a shaft housing portion;
a camshaft mounted for rotation in said body about a rotational axis and having a cam in said cam housing portion, said cam having a cam surface extending about the rotational axis at non-uniform radial distances from the rotational axis;
shafting extending along a longitudinal axis and mounted for reciprocation in said shaft housing portion of said body along said longitudinal axis, said shafting having a proximal end portion having a cam follower surface engageable with said cam, said shafting having a distal end portion including a cutter, said shafting comprising a cutter drive shaft and a cutter shaft;
said cutter drive shaft having a proximal end portion defining said cam follower surface and a distal end portion;
said cutter shaft having a proximal end portion and a distal end portion including said cutter; and
a connector selectively engaged between said distal end portion of said cutter drive shaft and said proximal end portion of said cutter shaft to selectively maintain a connection between said cutter drive shaft and said cutter shaft; and
wherein said shaft housing portion includes a wall defining an opening extending transversely therethrough, said opening positioned in general alignment with said connector to provide access to said connector to allow selective disengagement of said connector from between said distal end portion of said cutter drive shaft and disconnection of said cutter shaft from said cutter drive shaft; and wherein said connector is positioned within aligned openings in said distal end portion of said cutter drive shaft and said proximal end portion of said cutter shaft to maintain said connection between said cutter drive shaft and said cutter shaft.

19. The instrument of claim 18 and further comprising:
a rotary motor connected to said camshaft for rotating said camshaft.

20. The instrument of claim 19 and further comprising:
a controllable source of energy coupled to said rotary motor for energizing said rotary motor and controlling power applied to said rotary motor.

21. The instrument of claim 18 wherein said longitudinal axis is arranged transverse to said rotational axis.

22. The instrument of claim 18, further comprising a spring positioned in a spring housing portion of said body, said spring providing a biasing force to said shafting in a direction of said longitudinal axis toward said cutter to bias said cam follower surface of said shafting away from said cam surface to a disengaged position wherein said shafting is normally disengaged from said cam surface.

23. The instrument of claim 18, wherein said distal end portion of said cutter drive shaft and said proximal end portion of said cutter shaft include connection portions, said connection portions including an axial stem received within an axial bore to connect said cutter shaft to said cutter drive shaft.

24. The instrument of claim 23, wherein said distal end portion of said cutter drive shaft includes said axial bore and said proximal end portion of said cutter shaft includes said axial stem.

25. The instrument of claim 18, wherein said connector comprises a screw, and wherein one of said aligned openings is threaded, said screw threadedly engaged within said threaded opening to maintain said connection between said cutter drive shaft and said cutter shaft.

26. The instrument of claim 18, wherein said connector is positioned entirely within said shaft housing portion of said body.

27. The instrument of claim 18, wherein said connector comprises a screw having a threaded portion and a head portion, wherein one of said aligned openings is threaded, said threaded portion of said screw threadedly engaged within said threaded opening to maintain said connection between said cutter drive shaft and said cutter shaft, said head portion of said screw inwardly recessed from an inner wall of said shaft housing portion.

28. The instrument of claim 18, wherein said opening in said wall of said shaft housing portion comprises an elongate slot extending along said longitudinal axis.

29. The instrument of claim 18, further comprising a plurality of said cutter shafts, each of said plurality of cutter shafts having a different configuration of said cutter.

30. The instrument of claim 18, wherein said cutter shaft is slidably displaced along an axial bore defined by said shaft housing portion of said body.

31. A powered instrument for surgical use, comprising:
a body;
a camshaft mounted for rotation in said body about a rotational axis and including a cam having a cam surface extending about said rotational axis at non-uniform distances from the rotational axis;

shafting extending along a longitudinal axis and mounted for reciprocation in a shaft housing portion of said body along said longitudinal axis, said shafting having a proximal end portion having a cam follower surface engageable with said cam, said shafting having a distal end portion including a cutter, said rotational axis arranged transverse to said longitudinal axis of said shafting, said shafting comprising a cutter drive shaft and a cutter shaft;

said cutter drive shaft having a proximal end portion defining said cam follower surface and a distal end portion;

said cutter shaft having a proximal end portion and a distal end portion including said cutter; and a connector selectively engaged between said distal end portion of said cutter drive shaft and said proximal end portion of said cutter shaft to selectively maintain a connection between said cutter drive shaft and said cutter shaft; and wherein said shaft housing portion includes a wall defining an opening extending transversely therethrough, said opening positioned in general alignment with said connector to provide access to said connector to allow selective disengagement of said connector from between said distal end portion of said cutter drive shaft and said proximal end portion of said cutter shaft and disconnection of said cutter shaft from said cutter drive shaft; and wherein said connector is positioned within aligned openings in said distal end portion of said cutter drive shaft and said proximal end portion of said cutter shaft to maintain said connection between said cutter drive shaft and said cutter shaft.

32. The instrument of claim 31 and further comprising:
a spring in a spring housing portion of said body and normally holding said cam follower surface of said shafting disengaged from said cam surface.

33. The instrument of claim 31 and further comprising:
a rotary motor connected to said camshaft for rotating said camshaft about said rotational axis.

34. The instrument of claim 31, wherein said distal end portion of said cutter drive shaft and said proximal end portion of said cutter shaft include connection portions, said connection portions including an axial stem received within an axial bore to connect said cutter shaft to said cutter drive shaft.

35. The instrument of claim 34, wherein said distal end portion of said cutter drive shaft includes said axial bore and said proximal end portion of said cutter shaft includes said axial stem.

36. The instrument of claim 31, wherein said connector comprises a screw, and wherein one of said aligned openings is threaded, said screw threadedly engaged within said threaded opening to maintain said connection between said cutter drive shaft and said cutter shaft.

37. The instrument of claim 31, wherein said connector is positioned entirely within said shaft housing portion of said body.

38. The instrument of claim 31, wherein said connector comprises a screw having a threaded portion and a head portion, wherein one of said aligned openings is threaded, said threaded portion of said screw threadedly engaged within said threaded opening to maintain said connection between said cutter drive shaft and said cutter shaft, said head portion of said screw inwardly recessed from an inner wall of said shaft housing portion.

39. The instrument of claim 31, wherein said opening in said wall of said shaft housing portion comprises an elongate slot extending along said longitudinal axis.

40. The instrument of claim 31, further comprising a plurality of said cutter shafts, each of said plurality of cutter shafts having a different configuration of said cutter.

41. The instrument of claim 31, wherein said cutter shaft is slidably displaced along an axial bore defined by said shaft housing portion of said body.

* * * * *